United States Patent [19]

Marks

[11] 4,087,335

[45] May 2, 1978

[54] INHIBITORS FOR VINYLBENZYL CHLORIDE AND VINYLTOLUENE DECOMPOSITION

[75] Inventor: Allen P. Marks, Holland, Pa.

[73] Assignee: Rohm and Haas Company, Philadelphia, Pa.

[21] Appl. No.: 793,981

[22] Filed: May 5, 1977

Related U.S. Application Data

[63] Continuation-in-part of Ser. No. 615,146, Sep. 19, 1975, abandoned.

[51] Int. Cl.² .................. B01D 3/34; C07C 25/14; C07C 15/02
[52] U.S. Cl. .................. 203/6; 203/8; 203/9; 203/57; 203/60; 260/649 R; 260/666.5; 260/669 A
[58] Field of Search .................. 203/6, 7, 8, 9, 57, 203/60; 260/666.5, 669 A, 649 R

[56] References Cited

U.S. PATENT DOCUMENTS

| | | | |
|---|---|---|---|
| 2,399,340 | 4/1946 | Franz | 203/9 |
| 2,900,421 | 8/1959 | Kharasch et al. | 203/9 |
| 3,632,626 | 1/1972 | Schneller et al. | 260/669 A |
| 3,715,283 | 2/1973 | Bockmann | 203/6 |
| 3,919,054 | 11/1975 | Hands | 203/6 |

*Primary Examiner*—Wilbur L. Bascomb, Jr.

[57] ABSTRACT

A method is disclosed for stabilizing vinylbenzyl chloride and vinyltoluene against violent decomposition in the presence of iron and chlorine at ambient and above ambient temperatures which comprises contacting the vinylbenzyl chloride or vinyltoluene with an amount of a Lewis base sufficient to inhibit the decomposition during the preparation, purification or storage of said vinylbenzyl chloride or vinyltoluene.

10 Claims, No Drawings

INHIBITORS FOR VINYLBENZYL CHLORIDE AND VINYLTOLUENE DECOMPOSITION

This is a continuation-in-part of U.S. Ser. No. 615,146 filed Sept. 19, 1975 and now abandoned.

THE DISCLOSURE

This invention relates to a process for stabilizing vinylbenzyl chloride and vinyltoluene against violent decomposition.

It is known that vinylbenzyl chloride is a very useful monomer capable of entering into various reactions, including polymerizations, and is especially useful in the preparation of ion exchange resins. One process for the preparation of vinylbenzyl chloride involves the following reaction:

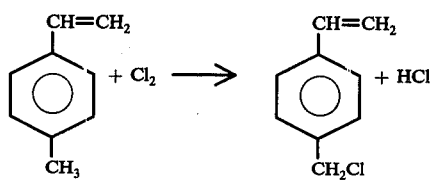

The two aromatic compounds in this sequence, the reactant vinyltoluene and the product vinylbenzyl chloride, in the presence of iron and chlorine, are subject to instantaneous and extremely violent decomposition or polymerization. This is manifested by a tremendous pressure buildup and large exotherm. This violent reaction not only causes irreversible loss of reactant and product, but is an extremely serious safety factor, since such decomposition, when confined, can occur with explosive violence.

The likelihood of iron contamination in commercial reactors and distillation apparatus is such that vinylbenzyl chloride is an extremely dangerous compound to process. Likewise, vinyltoluene in the presence of iron and hydrogen chloride or chlorine, such as would be present in the above-detailed reaction sequence, is equally dangerous. It is necessary, therefore, that effective means of preventing this violent decomposition be found in order to make it safe to process and store these compounds. The present invention provides a means whereby these compounds can be so stabilized that they can be safely processed and stored.

A method has been found for stabilizing vinylbenzyl chloride and vinyltoluene against violent decompositions in the presence of iron and chlorine at ambient and above ambient temperatures, which comprises contacting said vinylbenzyl chloride or vinyltoluene with an amount of a Lewis base selected from cyclic and acyclic amides and sulfoxides sufficient to inhibit decomposition thereof during the preparation, purification or storage of said vinylbenzyl chloride and vinyltoluene.

The mechanism by which vinylbenzyl chloride decomposes involves complex chemical considerations. Analysis of vinylbenzyl chloride which has been allowed to decompose or polymerize violently in the presence about 25 parts per million of ferric chloride shows that the monomer reacts mostly by way of a Friedel-Crafts reaction and also to a lesser extent by polymerization through the vinyl group. A pure Friedel-Crafts polymer should have no measurable chlorine content, as the Friedel-Crafts reaction proceeds by reaction through the —CH₂Cl group, liberating hydrogen chloride. The results show the presence of about 13.5% of chlorine in the elemental analysis of the polymerized product, taking into account the amount of chlorine present due to the ferric chloride. Further support for the assumption that the violent decomposition of vinylbenzyl chloride proceeds by a complex route, involving more than just a Friedel-Crafts polymerization, is supplied by the fact that a large percentage of the total weight of polymer can be selectively extracted and that vinyl polymers are more soluble than the highly crosslinked Friedel-Crafts polymers.

This complexity can be further appreciated from an examination of the decomposition of vinyltoluene. If vinyltoluene, or even styrene, is mixed with chlorine or hydrogen chloride in the presence of iron, a reaction as violent as that of vinylbenzyl chloride occurs. Vinyltoluene or styrene is not capable of a Friedel-Crafts reaction. The violent reaction occurs when there is less than 0.5% chlorinated material present in the reaction medium. Clearly, a chlorinated species is not the reacting agent, but it is the vinyltoluene or styrene itself.

The present invention is a process which prevents the dangerously violent exothermic polymerization of vinylbenzyl chloride and vinyltoluene, but which does not prevent the gradual decay of these compounds. Thus, in the presence of ferric chloride or iron and chlorine/hydrogen chloride, vinylbenzyl chloride and vinyltoluene, respectively, will not violently decompose at ambient and above ambient temperatures when this reaction is inhibited by Lewis bases. However, even in the presence of these compounds, the monomers will decay over a period of time.

It has been found that Lewis bases which interact through strong electrostatic forces are very effective in preventing the violent reaction, while those that interact by covalent forces, such as ketones, ethers, and so forth, are not very effective in this regard. The most effective of the former compounds are amines, cyclic and acyclic amides and sulfoxides. Thus, useful inhibitors of the violent decomposition of vinylbenzyl chloride and vinyltoluene include: caprolactam, lauryl lactam, dimethylformamide, formamide, n-butyl formamide, di-n-butyl formamide, benzamide, acetanilide, N,N-diethyl-toluamide, N-methyl-acetanilide, N-cyclohexyl formamide, N,N-methylene bis-acrylamide, naphthalene acetamide, trimethyl acetamide, stearamide, 4-picoline-N-oxide, pyridine N-oxide, pyrrolidone, methyl pyrrolidone, diethanol amine, dimethyl sulfoxide, di-n-butyl sulfoxide, di-phenyl sulfoxide, dibenzyl sulfoxide, and the like. These Lewis bases are useful in amounts ranging from 0.02% to about 0.05% by weight of monomer, and these quantities are sufficient to inhibit the violent decomposition of vinylbenzyl chloride and vinyltoluene in the presence of ferric chloride and chlorine/hydrogen chloride, respectively. Further, they are effective at ambient and above ambient temperatures. A further factor is that as the level of the Lewis bases is increased, higher levels of ferric chloride can be tolerated without explosive decomposition, thereby further increasing processing and handling safety.

The useful Lewis bases can be added directly to the reactants when the process involved is the preparation of vinylbenzyl chloride from vinyltoluene, or any other process whereby either compound is a reactant or product. Likewise, the bases can be added directly to crude, impure product streams prior to purification, as by distillation. In the latter situation, the compounds can also be added directly to the distillation column to prevent any decomposition therein. The compounds are also useful in preventing violent decomposition during storage of these compounds at ambient or above ambient temperatures.

As these Lewis bases are only effective to inhibit the violent decompositions of the monomers, other inhibitors must be employed to prevent the slow polymerization which the monomers undergo, even in the presence of the Lewis bases.

The process of the present invention can be more readily perceived from the following examples.

EXAMPLE I

This example shows the violence of the decomposition reaction. 0.2 ml of a saturated ferric chloride solution in ethylene dichloride is added to 10.0 ml of vinylbenzyl chloride in a 150 ml beaker. An instantaneous reaction occurs, generating an exotherm of about 100° C. with the evolution of copious amounts of hydrogen chloride and sending solid bits of polymer crashing against the top of the hood, about four feet high. This pressure buildup is also measured in a bombtype apparatus. The recorded pressure goes from 0 to 140 p.s.i.a. in less than a hundreth of a second, breaking the rupture disc (rated at 750 p.s.i.a.), indicating that the reaction proceeds much too rapidly for the instruments to record. It is found that vinylbenzyl chloride, when uninhibited, will react violently with as little as 0.0006% iron.

EXAMPLE II

To a flask containing vinyltoluene and hydrogen chloride is added 0.1% of ferric chloride by weight of vinyltoluene and 0.2% of caprolactam by weight of vinyltoluene. No violent reaction occurs throughout the temperature range of 25°–100° C. The same quantity of dimethylformamide gives the same results under the same conditions.

EXAMPLE III

To a flask containing vinylbenzyl chloride is added ferric chloride and a given inhibitor, and the flask is either held at ambient temperature or is heated to as high as 160° C. The results are given in Table I. The figures for "Iron" indicate the concentration of iron that is present when the levels of inhibitors indicated are tested. In all cases, the results indicate an effective inhibition of violent reaction.

TABLE I

| INHIBITOR | CONCENTRATION INHIBITOR | IRON | TEMPERATURE (° C.) |
|---|---|---|---|
| None | — | 0.001%[1] | 25 |
| Caprolactam | 0.20–0.2% | 0.01–0.1% | 25–160 |
| Lauryl lactam | 0.1–0.3% | 0.3–0.1% | 25–100 |
| Formamide | 0.1% | 0.01 | 25 |
| Dimethyl Formamide | 0.02–0.2% | 0.01–0.1% | 25–125 |
| n-Butyl Formamide | 0.1% | 0.02–0.04% | 25–80 |
| Di-n-Butyl Formamide | 0.1% | 0.02–0.03% | 25–80 |
| Benzamide | 0.1% | 0.02–0.04% | 25 |
| Acetanilide | 0.1% | 0.02–0.03% | 25 |
| N,N-Diethyl Toluamide | 0.1% | 0.04% | 25 |
| N-Methyl Acetanilide | 0.1% | 0.04% | 25 |
| N-Cyclohexyl Formamide | 0.1% | 0.05% | 25 |
| N,N-Methylene bis-Acrylamide | 0.1% | 0.05% | 25 |
| Naphthalene Acetamide | 0.1% | 0.03% | 25 |
| Trimethyl Acetamide | 0.1% | 0.06% | 25 |
| Pyrrolidone | 0.1% | 0.06% | 25–125 |
| N-Methyl Pyrrolidone | 0.1% | 0.06% | 25–125 |
| 4-Picoline-N-oxide | 0.2% | 0.01% | 25–140 |
| Pyridine N-oxide | 0.1% | 0.01% | 25–140 |
| Diethanol Amine | 0.1% | 0.01% | 25–150 |
| Dimethyl-Sulfoxide | 0.1–0.2% | 0.01–0.06% | 25–145 |
| Di-n-Butyl-Sulfoxide | 0.1% | 0.02–0.03% | 25–100 |
| Di-phenyl-Sulfoxide | 0.1–0.2% | 0.02–0.03% | 25 |
| Di-benzyl-Sulfoxide | 0.1–0.2% | 0.02% | 25–80 |

[1]Violent reaction upon, addition of ferric chloride.

EXAMPLE IV

Example III is repeated except that a monomer mix of 88% vinylbenzyl chloride and 12% divinyl benzene is used and covalently interacting bases are also tested. The results are given in Table II.

TABLE II

| INHIBITOR | CONCENTRATION INHIBITOR | IRON | RESULT |
|---|---|---|---|
| None | — | 0.001% | Violent Reaction |
| Acetone | 1.0% | 0.02% | Violent Reaction |
| Ethanol | 0.5% | 0.03% | Violent Reaction |
| Water | 15.0% (by vol.) | 0.03% | Violent Reaction |
| Dimethyl Formamide | 0.05% | 0.03% | No Reaction |

It is clear that vinylbenzyl chloride is effectively stabilized against violent decomposition by compounds interacting by electrostatic forces but not by compounds interacting by covalent forces.

EXAMPLE V

Three overhead streams from the vinyltoluene to vinylbenzyl chloride process are treated with caprolactam in varying concentration in the presence of varying levels of ferric chloride and at varying temperatures. The streams are as follows:

| | A | B | C |
|---|---|---|---|
| Vinyltoluene | 90.80% | 0.32% | 97.70% |
| α-Chlorovinyl Toluene | 5.10% | 1.37% | 0.41% |
| η-Chlorovinyl Toluene | 0.75% | 1.91% | — |
| Vinylbenzyl Chloride | 1.60% | 96.20% | 0.15% |
| Polymer | 0.04% | — | — |
| Nitrogen Level (% by weight) | 0.01% | 0.02% | — |
| Iron Level (% by weight) | 0.0002% | 0.0005% | 0.0001% |

The tests are performed in a stirred flask held for 2 hours at the indicated temperatures.

The results are summarized in Table III. The amounts of caprolactam used indicate recommended levels for effective inhibition of violent reaction.

TABLE III

| STREAM | TEMPERATURE (° C.) | CONCENTRATION CAPROLACTAM[1] | IRON[2] |
|---|---|---|---|
| A | 100 | 0.22% | 0.09% solubilized Fe |
| B | 125 | 0.24% | 0.08% solubilized Fe |
| C | 100 | 0.18% | 0.08% solubilized Fe |

[1]This amount of caprolactam is added to the streams in addition to any other inhibitor already present (such as to prevent the slow polymerization of the vinyl compounds)

[2]These concentrations are for the final resultant solution determined directly by analysis of the final solution. The iron is added to streams at ambient temperature and then the stream is brought to the indicated temperature.

EXAMPLE VI

Vinylbenzyl chloride to which are added 0.4% ferric chloride and 0.1% caprolactam is allowed to stand at ambient temperature for a period of time. A gradual buildup of polymer is observed as follows:

| MINUTES AFTER ADDITION OF FeCl$_3$ | % POLYMER |
|---|---|
| 0 | 0.0 |
| .5 | 3.3 |
| 50 | 4.1 |
| 140 | 6.5 |
| 445 | 36.0 |
| 1440 | 59.0 |

This example shows that while no violent reaction is observed, a gradual polymer buildup occurs, without a significant exotherm and probably via a cationic-vinyl polymerization route. Thus, after 24 hours, over half the vinylbenzyl chloride has polymerized. This gradual polymerization is not inhibited by the disclosed inhibitors, and must be inhibited by other means.

I claim:

1. A method for stabilizing a compound selected from vinylbenzyl chloride and vinyltoluene against violent decomposition in the presence of iron and chlorine at ambient and above ambient temperatures, which comprises contacting said compound with an amount of a Lewis base selected from cyclic and acyclic amides and sulfoxides sufficient to inhibit said violent decomposition thereof during the preparation, purification or storage of said vinylbenzyl chloride or vinyltoluene.

2. The method of claim 1, where the purification is by distillation.

3. The method of claim 1, where the Lewis base is employed in an amount of from 0.01% to 0.5% by weight based upon the weight of the compound to be stabilized.

4. The method of claim 1, where the Lewis base is employed in an amount of from 0.1% to 0.3% by weight based upon the weight of the compound to be stabilized.

5. The method of claim 3, where the Lewis base is N,N-diethyl toluamide.

6. The method of claim 4, where the Lewis base is caprolactam.

7. The method of claim 4, where the Lewis base is dimethylformamide.

8. The method of claim 1 where the Lewis base is added to crude impure streams of vinylbenzyl chloride prior to distillation.

9. The method of claim 7, where the Lewis base is further added to the distillation column prior to distillation.

10. The method of claim 1, where the Lewis base is added directly to vinyltoluene during the preparation of vinylbenzyl chloride therefrom.

* * * * *

UNITED STATES PATENT AND TRADEMARK OFFICE
CERTIFICATE OF CORRECTION

PATENT NO. : 4,087,335
DATED : May 2, 1978
INVENTOR(S) : Allen P. Marks

It is certified that error appears in the above-identified patent and that said Letters Patent are hereby corrected as shown below:

Column 4, line 56 - "$\eta$-Chlorovinyl" should read -- p-Chlorovinyl --

Column 5, line 27, under column headed "Minutes After Addition of $FeCl_3$" - ".5" should read -- 5 -- (no decimal point).

Signed and Sealed this

Ninth Day of October 1979

[SEAL]

Attest:

RUTH C. MASON
Attesting Officer

LUTRELLE F. PARKER
Acting Commissioner of Patents and Trademarks